United States Patent [19]

Ryder et al.

[11] 4,302,664
[45] Nov. 24, 1981

[54] CONTACT LENS ASEPTOR

[75] Inventors: Francis E. Ryder; Michael D. Thomas, both of Arab, Ala.

[73] Assignee: Ryder International Corporation, Arab, Ala.

[21] Appl. No.: 112,783

[22] Filed: Jan. 16, 1980

[51] Int. Cl.³ .......................... A61L 2/04; H05B 1/02
[52] U.S. Cl. .................................. 219/504; 219/505; 219/521; 422/307
[58] Field of Search .............. 219/449, 494, 504, 505, 219/521, 385; 422/109, 300, 302, 307, 292

[56] References Cited

U.S. PATENT DOCUMENTS

| | | | |
|---|---|---|---|
| 3,070,105 | 12/1962 | Brown | 206/5.1 X |
| 3,400,252 | 9/1968 | Hayakawa et al. | 219/504 |
| 3,524,455 | 8/1970 | Hoogesteger et al. | 206/5.1 X |
| 3,876,861 | 4/1975 | Wightman et al. | 219/504 X |
| 3,998,590 | 12/1976 | Glorieux | |
| 4,044,226 | 8/1977 | Kadlecik et al. | 219/521 |
| 4,178,499 | 12/1979 | Bowen | 219/521 X |

FOREIGN PATENT DOCUMENTS 1051578 12/1966 United Kingdom ................ 219/521

*Primary Examiner*—Arnold Turk
*Attorney, Agent, or Firm*—Trexler, Bushnell & Wolters, Ltd.

[57] ABSTRACT

A contact lens disinfector has a molded plastic casing with wells at opposite ends for receiving the respective lenses and the disinfecting solution. Caps are removably threaded onto the casing over the wells. A thermistor heater is embedded in the casing between the wells to provide a low temperature (60° C. -80° C.) heater for the solution for an extended heating cycle, thereby to inhibit deterioration of the lenses due to loss of transparency.

5 Claims, 4 Drawing Figures

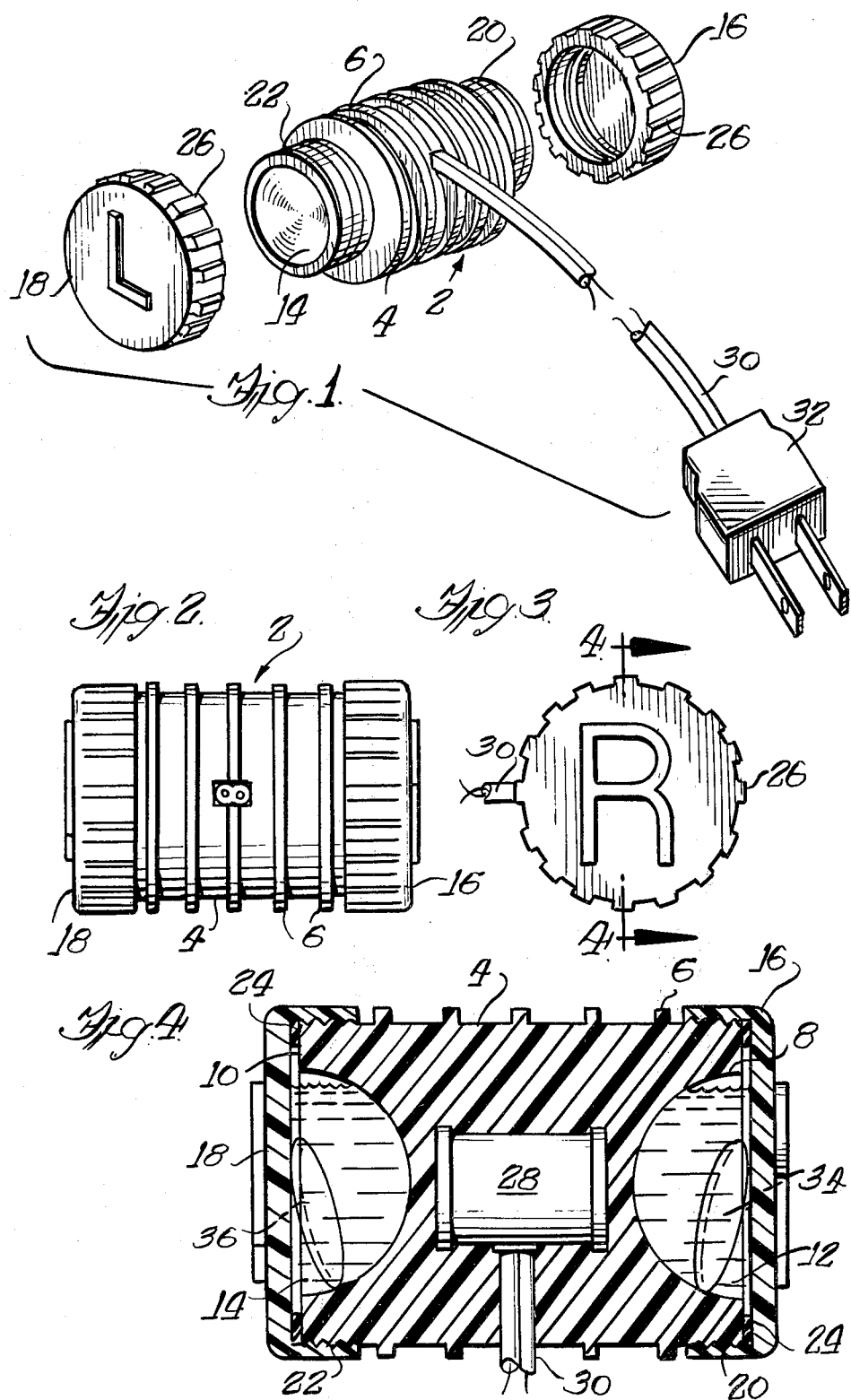

CONTACT LENS ASEPTOR

BACKGROUND OF THE INVENTION

This invention relates to aseptors or disinfectors for small objects such as contact lenses and the like.

Hydrophilic contact lenses, sometimes referred to as soft contact lenses, must be periodically disinfected or asepticized. Customarily, this asepticizing action is carried out by heating the lenses to a sufficient temperature and for a sufficient period of time in a aqueous saline solution. Various contact lens sterilizers or asepticizers which have been offered for sale accomplished this task. However, many of these units are designed to asepticize the lenses quickly, and for that reason they tend to apply a relatively high temperature to the lenses for a short period of time.

While the foregoing procedure is seemingly a timesaver to the user, the use of high temperatures in the disinfecting process tends to deteriorate the lenses. In this regard it has been found that over a period of time the lenses tend to become less transparent, thus taking on a cloudy appearance. Accordingly, the preferred disinfecting procedure is one in which a lesser temperature is used but for a somewhat longer period of time. Thus, it appears that while many prior art disinfectors utilize temperatures which are near the boiling point of the disinfectant solution (in the order of 100° C.) the preferred "heat history" of the disinfecting cycle is one in which the temperature is in the range of 60° C.–80° C.

OBJECTS AND SUMMARY OF THE INVENTION

An object of this invention is to provide a contact lens aseptor which reduces the temperature or "heat history" of the lenses during the disinfecting cycle, thereby to avoid deterioration of the lenses as to their transparency.

A further object of this invention is to provide an aseptor of the type stated which is compact and is relatively inexpensive to fabricate and at the same time embodies a heater which limits the disinfecting temperature to well below the boiling point of the disinfecting solution.

In accordance with the foregoing objects the aseptor comprises a casing having a pair of wells for receiving disinfecting solution, each well having an opening at the surface of the casing, a removable liquid-tight cover across each opening, means associated with each well respectively for providing indicia as to right or left eye contact lens, and an electrical heater embedded in said casing for supplying heat to the wells, said heater being of the type having a resistance that increases as a function of temperature to limit the maximum operating temperature of the heater.

The operating temperature of the heater is limited so that the operating temperature of the disinfecting solution in the wells is about 60° C. to about 80° C. In a preferred embodiment of the invention, the heater comprises a thermistor.

BRIEF DESCRIPTION OF THE FIGURES

FIG. 1 is an exploded perspective view of a contact lens aseptor constructed in accordance with and embodying the present invention;

FIG. 2 is a side elevational view of the aseptor;

FIG. 3 is a front view of the aseptor looked at from the right hand side of FIG. 2; and FIG. 4 is a sectional view taken along lines 4—4 of FIG. 3 and showing disinfecting solution and the contact lenses within the wells of the unit.

DETAILED DESCRIPTION

Referring now in more detail to the drawing there is shown a disinfectant unit or aseptor 2 comprising a one piece casing 4 of any suitable plastic material, such as a thermosetting resin. The casing 4 is of cylindrical form and has a number of axially spaced ribs 6 in the form of cylindrical rings and which serve as cooling fins that permit handling of the casing 4 when the latter is hot, as will be presently more fully described. The casing 4 furthermore has opposite axial ends 8,10, and at each of the ends 8,10 there is a recess or well 12,14 of substantially hemispherical shape. The wells open up at the surfaces of the casing that are at the ends 8,10.

For closing off each well 12,14 there is a threaded cap 16,18. Each cap 16,18 has an annular threaded skirt for engagement with external threads 20,22 on the casing 4 adjacent to the ends 8,10. The casing 4 or the caps 16,18 may each include an annular gasket 24 to provide a seal between the cap and the casing. The cap 18 is molded with a letter L while the cap 16 is molded with an R whereby suitable indicia are provided for indicating whether the right or left eye contact lens is in the associated well 12,14, as the case may be. Furthermore, the caps 16,18 may be formed with axial ribs 26 on the exterior of the cap skirts to facilitate manipulation of the caps. Integrally molded with and thus embedded in the casing 4 is a resistance heater 28 of the type having a resistance that increases as the function of temperature to limit the maximum operating temperature of the heater and to prevent a "runaway" condition. Such a heater 28 may be a thermistor. Devices of this type are known in the art and are characterized in that there is a change in the resistivity of a semi-conductor upon a change in its temperature. The thermistor heater 28 is fully embedded within the casing 4 and is axially disposed between the wells 12,14, as best shown in FIG. 4. The heater 28 includes insulated conductors in the form of a power line cord 30 that extends through the casing 4 and outwardly thereof for connection to a plug 32. The plug 32 is conventional and is to be plugged into a power line receptacle.

The operation of the unit 2 is apparent. Suffice to say, however, that the wells 12,14 may be filled with disinfecting solution and the contact lenses 34,36 deposited therein and with the caps 16,18 threaded in place as shown in FIG. 4. The heater 28 is of a type that gradually increases the temperature of the disinfecting solution in each well to about 60° C.–80° C., which constitutes a heat or temperature plateau that is maintained throughout the heating cycle. The temperature of the disinfecting solution should reach 80° C. for at least 10 minutes in order to provide a satisfactory disinfecting action.

The invention is claimed as follows:

1. A contact lens aseptor, comprising: an elongate molded plastic casing having a pair of wells at opposite ends thereof for receiving a contact lens and a quantity of disinfecting solution, each well opening to an end surface of the casing and removable cover means attachable to said casing at each end thereof to overlie the associated well opening, an electrical heater means integrally molded as a component of said casing and disposed intermediate said wells for supplying heat to each said well, the plastic material forming said casing being continuous from said heater to said wells, whereby said heater means is embedded in said casing, and said heater means being of a type having a resistance that increases as a function of temperature to limit the maximum operating temperature thereof, and power supply means affixed to said heater means and extending from said heater means to the exterior of said casing for connection to a source of power.

2. A contact lens aseptor according to claim 1 in which there are outwardly projecting fins on the casing to facilitate handling of the casing when the latter is hot.

3. A contact lens aseptor according to claim 1, further including means associated with each well respectively for providing indicia as to right or left eye contact lens.

4. A contact lens aseptor according to claim 1 in which the operating temperature of the solution in the wells is about 60° C. to 80° C.

5. A contact lens aseptor according to claim 1 or claim 4 in which said heater means comprises a thermistor.

* * * * *